US012766080B2

(12) United States Patent
Chang et al.

(10) Patent No.: US 12,766,080 B2
(45) **Date of Patent: *Oct. 20, 2026**

(54) PERSONAL CARE COMPOSITION PRESERVATIVES LEVEL OPTIMIZATION

(71) Applicant: The Procter & Gamble Company, Cincinnati, OH (US)

(72) Inventors: Debora W. Chang, Mason, OH (US); Eric Scott Johnson, Hamilton, OH (US); Matthew Francis Kuhar, Cincinnati, OH (US); Beth Anne Muir, Tipp City, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 889 days.

This patent is subject to a terminal disclaimer.

(21) Appl. No.: 17/980,169

(22) Filed: Nov. 3, 2022

(65) Prior Publication Data

US 2023/0062740 A1 Mar. 2, 2023

Related U.S. Application Data

(62) Division of application No. 17/078,813, filed on Oct. 23, 2020, now Pat. No. 11,523,979.

(60) Provisional application No. 62/925,511, filed on Oct. 24, 2019.

(51) Int. Cl.

| | |
|---|---|
| ***A61K 8/368*** | (2006.01) |
| ***A61K 8/365*** | (2006.01) |
| ***A61K 8/46*** | (2006.01) |
| ***A61K 8/73*** | (2006.01) |
| ***A61K 8/81*** | (2006.01) |
| ***A61Q 5/00*** | (2006.01) |
| ***A61Q 5/02*** | (2006.01) |

(52) U.S. Cl.

CPC .............. *A61K 8/368* (2013.01); *A61K 8/365* (2013.01); *A61K 8/463* (2013.01); *A61K 8/731* (2013.01); *A61K 8/737* (2013.01); *A61K 8/8147* (2013.01); *A61K 8/8152* (2013.01); *A61K 8/8158* (2013.01); *A61Q 5/006* (2013.01); *A61Q 5/02* (2013.01); *A61K 2800/30* (2013.01); *A61K 2800/48* (2013.01); *A61K 2800/524* (2013.01); *A61K 2800/5426* (2013.01)

(58) Field of Classification Search

None

See application file for complete search history.

(56) References Cited

U.S. PATENT DOCUMENTS

| | | | |
|---|---|---|---|
| 6,113,931 A | 9/2000 | Bonda et al. | |
| 6,147,038 A | 11/2000 | Halloran | |
| 9,610,234 B2 | 4/2017 | Mann et al. | |
| 9,890,107 B2 | 2/2018 | Schuch et al. | |
| 10,391,046 B2 | 8/2019 | Hartnett et al. | |
| 11,523,979 B2 | 12/2022 | Chang et al. | |
| 2002/0165283 A1 | 11/2002 | Lutz | |
| 2004/0234484 A1 | 11/2004 | Peffly | |
| 2006/0171911 A1 | 8/2006 | Schwartz et al. | |
| 2007/0020220 A1 | 1/2007 | Osborne | |
| 2007/0202069 A1 | 8/2007 | Tamareselvy | |
| 2008/0145328 A1 | 6/2008 | Schwartz et al. | |
| 2008/0206179 A1 | 8/2008 | Peffly | |
| 2009/0169644 A1 * | 7/2009 | Goddinger | A61Q 5/02 514/159 |
| 2009/0221463 A1 | 9/2009 | Kitko | |
| 2012/0213725 A1 * | 8/2012 | Galleguillos | C08K 5/0008 510/476 |
| 2015/0297489 A1 | 10/2015 | Kleinen et al. | |
| 2015/0328135 A1 | 11/2015 | Argembeaux et al. | |
| 2016/0015615 A1 | 1/2016 | Mann et al. | |
| 2017/0000710 A1 | 1/2017 | Klug et al. | |
| 2017/0239155 A1 | 8/2017 | Hartnett | |
| 2017/0333320 A1 | 11/2017 | Carnali et al. | |
| 2018/0311135 A1 | 11/2018 | Chang et al. | |
| 2019/0105247 A1 | 4/2019 | Song et al. | |
| 2019/0167554 A1 | 6/2019 | Wankhade | |
| 2019/0328647 A1 | 10/2019 | Chang et al. | |
| 2021/0121381 A1 | 4/2021 | Chang et al. | |
| 2021/0121382 A1 | 4/2021 | Chang et al. | |
| 2021/0186839 A1 | 6/2021 | Kroger Lyons et al. | |

FOREIGN PATENT DOCUMENTS

| | | |
|---|---|---|
| CN | 102114238 A | 7/2011 |
| CN | 103251529 A | 8/2013 |
| CN | 105832880 A | 8/2016 |
| CN | 107198674 A | 9/2017 |
| CN | 109662927 B | 11/2021 |
| EP | 2786742 A1 | 10/2014 |
| JP | S61238716 A | 10/1986 |

(Continued)

OTHER PUBLICATIONS

PCT Search Report and Written Opinion for PCT/US2020/070689 dated Feb. 23, 2021, 20 pages.

(Continued)

*Primary Examiner* — David J Blanchard

*Assistant Examiner* — Sarah J Chickos

(74) *Attorney, Agent, or Firm* — Linda M. Sivik

(57) ABSTRACT

The present invention is direct to a hair care composition comprising from about 8 to about 17% of one or more surfactants; from about 0.1-0.25% of salicylate salts or acids; from about 0.1-0.25% of benzoate salts or acids wherein there is a weight ratio of about 1:1 to 2.5:1 for the salicylate salts or acids to sodium benzoate salts or acids.

52 Claims, No Drawings

(56) References Cited

FOREIGN PATENT DOCUMENTS

| | | | |
|---|---|---|---|
| JP | H08310925 | A | 11/1996 |
| JP | 2007153791 | A | 6/2007 |
| JP | 2016030722 | A | 3/2016 |
| WO | 2012017091 | A2 | 2/2012 |
| WO | 2012052536 | A2 | 4/2012 |

OTHER PUBLICATIONS

All Office Actions; U.S. Appl. No. 17/078,781, filed Oct. 23, 2020.
All Office Actions; U.S. Appl. No. 17/078,796, filed Oct. 23, 2020.
All Office Actions; U.S. Appl. No. 17/126,369, filed Dec. 18, 2020.
All Office Actions; U.S. Appl. No. 17/980,199, filed Nov. 3, 2022.
All Office Actions; U.S. Appl. No. 17/078,813, filed Oct. 23, 2020.
Document D5, OECD Guideline for Testing of Chemicals, Ready Biodegradability, vol. 301, Jul. 17, 1992, 62 pages.
Document D6, OK Compost and Seedling, 3 pages. (No date available).
U.S. Appl. No. 17/980,199, filed Nov. 3, 2022 to Debora W. Chang et al.

* cited by examiner

PERSONAL CARE COMPOSITION PRESERVATIVES LEVEL OPTIMIZATION

FIELD OF THE INVENTION

The present invention relates to hair care compositions comprising a preservative demonstrating efficacious microbial preservation in personal care compositions at lower preservative levels.

BACKGROUND OF THE INVENTION

A preservative is a substance that is added to personal care compositions, such as shampoos, body washes, body lotions, ointments, creams and salves, in order to inhibit microbial growth that may, for example, arise from contamination by the consumer when in use. Inhibiting the growth of bacteria, fungi and other microorganisms is paramount to maintaining product quality, extending the shelf life, and protecting the consumer. There is a continuous consumer preference for the reduction of the amount of preservatives used in consumer products. On the other hand, exposure of microorganisms to insufficient levels of preservatives or antimicrobials could potentially lead to the selection or emergence of resistant strains. Therefore, the need exists to use high enough levels of preservatives to inhibit microbial growth and maintain product quality but low enough to alleviate consumer concerns.

It has surprisingly been found that unprecedented low levels of sodium benzoate and sodium salicylate can provide efficacious microbial preservation in personal care compositions while also addressing consumer demand for lower preservative levels.

SUMMARY OF THE INVENTION

The present invention is direct to a hair care composition comprising from about 10 to about 17% of one or more surfactants; from about 0.1-0.25% of salicylate salts or acids; from about 0.1-0.25% of benzoate salts or acids wherein there is a weight ratio of about 1:1 to 2.5:1 for the salicylate salts or acids to sodium benzoate salts or acids.

These and other features, aspects, and advantages of the present invention will become evident to those skilled in the art from a reading of the present disclosure.

DETAILED DESCRIPTION OF EMBODIMENTS OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application," as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

The term "preservation" in the context of the present invention refers to the prevention or retardation of product deterioration due to microorganisms present in the product or composition. A "preservative agent" or "preservative" in the context of the present invention is a substance that prevents or retards the growth of microorganisms in a product or composition.

While the specification concludes with claims particularly pointing out and distinctly claiming the invention, it is believed that the present invention will be better understood from the following description.

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the hair care composition.

As used herein, "personal care compositions" includes products such as shampoos, shower gels, liquid hand cleansers, hair colorants, facial cleansers, and other surfactant-based liquid compositions.

As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Preservative

The composition also comprises one or more of a preservative. Each single preservative may be present from about 0.1% to about 0.25%, from about 0.1% to about 0.2%, from about 0.1-0.18%, by weight of the composition. The preservative may have a low log S water solubility of less than 0 or a high log S water solubility of 0 or greater. A preservative may have a low log S water solubility of less than 0 to about −5.0. A preservative may have a high log S water solubility of 0 to about 1.0. Additionally, combinations of high and low log S water solubility preservatives may be used.

Non limiting examples of preservatives may be salicylate salts or acids, benzoate salts or acids. Non-limiting examples of preservatives may be sodium salicylate, sodium benzoate, potassium salicylate, potassium benzoate, salicylic acid, benzoic acid, MEA-salicylate, MEA-benzoate, TEA-salicylate, TEA-benzoate, calcium salicylate, calcium benzoate, magnesium salicylate, magnesium benzoate, titanium salicylate, titanium benzoate, silver salicylate, silver benzoate, ammonium salicylate, ammonium benzoate, zinc salicylate, zinc benzoate, and combinations thereof.

The composition may comprise a weight ratio of salicylate salt or acid to benzoate salt or acid of 1:1 to 2.5:1; 1:1 to 2:1; 1:1 to 1.5:1; 1:0.9 to 2:1; 1:0.8 to 2:1; 1:0.75 to 2:1; 1:0.8 to 1.5:1.

Some suitable examples of low log S water solubility preservatives include metal pyrithiones, organic acids (including but not limited to: undecylenic acid, salicylic acid, dehydroacetic acid, sorbic acid), glycols (including but not limited to: caprylyl glycol, decline glycol), parabens, methylchloroisothiazolinone, benzyl alcohol, ethylenediaminetetraacetic acid, and combinations thereof. Examples of commercially available low log S water solubility preservative systems are provided under the tradenames Geogard 111 A™, Geoagard221A™, Mikrokill COS™, Mikrokill ECT™, and Glycacil™. Suitable examples of high log S water solubility preservatives can include sodium benzoate, methylisothiazolinone, DMDM hydantoin, and combinations thereof.

Detersive Surfactant

The hair care composition may comprise greater than 10% by weight of a surfactant system which provides cleaning performance to the composition. The surfactant system can include one or more surfactants. The one or more surfactants can be sulfate-based surfactants and/or substantially free of sulfate-based surfactants. The surfactants can be selected from anionic surfactants, amphoteric surfactants, zwitterionic surfactants, non-ionic surfactants, and combinations thereof. Various examples and descriptions of detersive surfactants are set forth in U.S. Pat. No. 8,440,605; U.S. Patent Application Publication No. 2009/155383; and U.S. Patent Application Publication No. 2009/0221463, which are incorporated herein by reference in their entirety. "Substantially free" of sulfate-based surfactants as used herein means from about 0 wt % to about 3 wt %, alternatively from about 0 wt % to about 2 wt %, alternatively from about 0 wt % to about 1 wt %, alternatively from about 0 wt % to about 0.5 wt %, alternatively from about 0 wt % to about 0.25 wt %, alternatively from about 0 wt % to about 0.1 wt %, alternatively from about 0 wt % to about 0.05 wt %, alternatively from about 0 wt % to about 0.01 wt %, alternatively from about 0 wt % to about 0.001 wt %, and/or alternatively free of sulfates. As used herein, "free of" means 0 wt %.

The hair care composition may comprise from about 10% to about 17%, from about 10% to about 16%, from about 10% to about 15%, from about 10% to about 14%, from about 10% to about 13% by weight of one or more surfactants.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the hair care composition include ammonium lauryl sulfate, ammonium laureth sulfate, ammonium C10-15 pareth sulfate, ammonium C10-15 alkyl sulfate, ammonium C11-15 alkyl sulfate, ammonium decyl sulfate, ammonium deceth sulfate, ammonium undecyl sulfate, ammonium undeceth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, sodium C10-15 pareth sulfate, sodium C10-15 alkyl sulfate, sodium C11-15 alkyl sulfate, sodium decyl sulfate, sodium deceth sulfate, sodium undecyl sulfate, sodium undeceth sulfate, potassium lauryl sulfate, potassium laureth sulfate, potassium C10-15 pareth sulfate, potassium C10-15 alkyl sulfate, potassium C11-15 alkyl sulfate, potassium decyl sulfate, potassium deceth sulfate, potassium undecyl sulfate, potassium undeceth sulfate, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, and combinations thereof. The anionic surfactant may be sodium lauryl sulfate or sodium laureth sulfate.

The composition of the present invention can also include anionic surfactants selected from the group consisting of:

a) $R_1O(CH_2CHR_3O)_ySO_3M$;

b) $CH_3(CH_2)_zCHR_2CH_2O(CH_2CHR_3O)_ySO_3M$; and c) mixtures thereof, where $R_1$ represents $CH_3(CH_2)_{10}$, $R_2$ represents H or a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not zero (0), and M is a monovalent or divalent, positively-charged cation.

Suitable anionic alkyl sulfates and alkyl ether sulfate surfactants include, but are not limited to, those having branched alkyl chains which are synthesized from C8 to C18 branched alcohols which may be selected from the group consisting of: Guerbet alcohols, aldol condensation derived alcohols, oxo alcohols, F-T oxo alcohols and mixtures thereof. Non-limiting examples of the 2-alkyl branched alcohols include oxo alcohols such as 2-methyl-1-undecanol, 2-ethyl-1-decanol, 2-propyl-1-nonanol, 2-butyl 1-octanol, 2-methyl-1-dodecanol, 2-ethyl-1-undecanol, 2-propyl-1-decanol, 2-butyl-1-nonanol, 2-pentyl-1-octanol, 2-pentyl-1-heptanol, and those sold under the tradenames LIAL® (Sasol), ISALCHEM® (Sasol), and NEODOL® (Shell), and Guerbet and aldol condensation derived alcohols such as 2-ethyl-1-hexanol, 2-propyl-1-butanol, 2-butyl-1-octanol, 2-butyl-1-decanol, 2-pentyl-1-nonanol, 2-hexyl-1-octanol, 2-hexyl-1-decanol and those sold under the tradename ISOFOL® (Sasol) or sold as alcohol ethoxylates and alkoxylates under the tradenames LUTENSOL XP® (BASF) and LUTENSOL XL® (BASF).

The anionic alkyl sulfates and alkyl ether sulfates may also include those synthesized from C8 to C18 branched alcohols derived from butylene or propylene which are sold under the trade names EXXAL™ (Exxon) and Marlipal® (Sasol). This includes anionic surfactants of the subclass of sodium trideceth-n sulfates (STnS), where n is between about 0.5 and about 3.5. Exemplary surfactants of this subclass are sodium trideceth-2 sulfate and sodium trideceth-3 sulfate. The composition of the present invention can also include sodium tridecyl sulfate.

Surfactants that are substantially free of sulfates and suitable for use in the compositions can include sodium, ammonium or potassium salts of isethionates; sodium, ammonium or potassium salts of sulfonates; sodium, ammonium or potassium salts of ether sulfonates; sodium, ammonium or potassium salts of sulfosuccinates; sodium, ammonium or potassium salts of sulfoacetates; sodium, ammonium or potassium salts of sulfolaurates; sodium, ammonium or potassium salts of glycinates; sodium, ammonium or potassium salts of sarcosinates; sodium, ammonium or potassium salts of glutamates; sodium, ammonium or potassium salts of alaninates; sodium, ammonium or potassium salts of carboxylates; sodium, ammonium or potassium salts of taurates; sodium, ammonium or potassium salts of phosphate esters; and combinations thereof.

The surfactant system can include one or more amino acid based anionic surfactants. Non-limiting examples of amino acid based anionic surfactants can include sodium, ammonium or potassium salts of acyl glycinates; sodium, ammonium or potassium salts of acyl sarcosinates; sodium, ammonium or potassium salts of acyl glutamates; sodium, ammonium or potassium salts of acyl alaninates and combinations thereof.

The amino acid based anionic surfactant can be a glutamate, for instance an acyl glutamate. Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium caproyl glutamate, disodium caproyl glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl Glutamate, sodium olivoyl glutamate, disodium olivoyl glutamate, sodium palmoyl glutamate, disodium palmoyl Glutamate, TEA-cocoyl glutamate, TEA-hydrogenated tallowoyl glutamate, TEA-lauroyl glutamate, and mixtures thereof.

The amino acid based anionic surfactant can be an alaninate, for instance an acyl alaninate. Non-limiting example of acyl alaninates can include sodium cocoyl alaninate, sodium lauroyl alaninate, sodium caproyl alaninate, sodium N-dodecanoyl-l-alaninate and combination thereof.

The amino acid based anionic surfactant can be a sarcosinate, for instance an acyl sarcosinate. Non-limiting examples of sarcosinates can be selected from the group consisting of sodium lauroyl sarcosinate, sodium cocoyl sarcosinate, sodium myristoyl sarcosinate, sodium caproyl sarcosinate, TEA-cocoyl sarcosinate, ammonium cocoyl sarcosinate, ammonium lauroyl sarcosinate, dimer dilinoleyl bis-lauroylglutamate/lauroylsarcosinate, disodium lauroamphodiacetate lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

The amino acid based anionic surfactant can be a glycinate for instance an acyl glycinate. Non-limiting example of acyl glycinates can include sodium cocoyl glycinate, sodium lauroyl glycinate and combination thereof.

The composition can contain anionic surfactants selected from the group consisting of sulfosuccinates, isethionates, sulfonates, sulfoacetates, sulfolaurates, glucose carboxylates, alkyl ether carboxylates, acyl taurates, lactates, lactylates and mixture thereof.

The composition of the present invention can also include anionic alkyl and alkyl ether sulfosuccinates and/or dialkyl and dialkyl ether sulfosuccinates and mixtures thereof. The dialkyl and dialkyl ether sulfosuccinates may be a C6-15 linear or branched dialkyl or dialkyl ether sulfosuccinate. The alkyl moieties may be symmetrical (i.e., the same alkyl moieties) or asymmetrical (i.e., different alkyl moieties). Nonlimiting examples include: disodium lauryl sulfosuccinate, disodium laureth sulfosuccinate, sodium bistridecyl sulfosuccinate, sodium dioctyl sulfosuccinate, sodium dihexyl sulfosuccinate, sodium dicyclohexyl sulfosuccinate, sodium diamyl sulfosuccinate, sodium diisobutyl sulfosuccinate, linear bis(tridecyl) sulfosuccinate and mixtures thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof.

Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride. Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sulfonates can include alpha olefin sulfonates, linear alkylbenzene sulfonates, alkyl glyceryl sulfonates, sodium laurylglucosides hydroxypropylsulfonate and combination thereof.

Non-limiting examples of sulfoacetates can include sodium lauryl sulfoacetate, ammonium lauryl sulfoacetate and combination thereof.

Non-limiting examples of sulfolaurates can include sodium methyl-2 sulfolaurate, disodium sulfolaurate and combinations thereof.

Non-limiting example of glucose carboxylates can include sodium lauryl glucoside carboxylate, sodium cocoyl glucoside carboxylate and combinations thereof.

Non-limiting example of alkyl ether carboxylate can include sodium laureth-4 carboxylate, laureth-5 carboxylate, laureth-13 carboxylate, sodium C12-13 pareth-8 carboxylate, sodium C12-15 pareth-8 carboxylate and combination thereof.

Non-limiting example of acyl taurates can include sodium methyl cocoyl taurate, sodium methyl lauroyl taurate, sodium caproyl methyltaurate, sodium methyl oleoyl taurate, sodium cocoyl taurate, sodium lauroyl taurate, sodium caproyl taurate, and combination thereof.

Non-limiting example of lactates can include sodium lactate.

Non-limiting examples of lactylates can include sodium lauroyl lactylate, sodium cocoyl lactylate, and combination thereof.

The hair care composition may comprise a co-surfactant. The co-surfactant can be selected from the group consisting of amphoteric surfactant, zwitterionic surfactant, non-ionic surfactant and mixtures thereof. The co-surfactant surfactant can be selected from the group consisting of betaines, propionates, sultaines, hydroxysultaines, amphohydroxypropyl sulfonates, alkyl amphoacetates, alkyl amphodiacetates, and combination thereof. The co-surfactant can include, but is not limited to, lauramidopropyl betaine, cocamidopropyl betaine, coco-betaine, cetyl betaine, lauryl hydroxysultaine, sodium lauroamphoacetate, disodium cocoamphodiacetate, cocamide monoethanolamide and mixtures thereof.

The hair care composition may further comprise from about 0.25% to about 15%, from about 0.5% to about 15%, from about 1% to about 14%, from about 2% to about 13% by weight of one or more amphoteric, zwitterionic, nonionic co-surfactants, or a mixture thereof.

Suitable amphoteric or zwitterionic surfactants for use in the hair care composition herein include those which are known for use in shampoo or other hair care cleansing. Non limiting examples of suitable zwitterionic or amphoteric surfactants are described in U.S. Pat. Nos. 5,104,646 and 5,106,609, which are incorporated herein by reference in their entirety.

Amphoteric co-surfactants suitable for use in the composition include those surfactants described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable amphoteric surfactant include, but are not limited to, those selected from the group consisting of: sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphodiacetate, ammonium cocoamphohydroxypropylsulfonate, ammonium cocoamphopropionate, ammonium cornamphopropionate, ammonium lauraminopropionate, ammonium lauroamphoacetate, ammonium lauroamphodiacetate, ammonium lauroamphohydroxypropylsulfonate, ammonium lauroamphopropionate, ammonium cornamphopropionate, ammonium lauriminodipropionate, triethanolamine cocaminopropionate, triethanolamine cocaminodipropionate, triethanolamine cocoamphoacetate, triethanolamine cocoamphohydroxypropylsulfonate, triethanolamine cocoamphopropionate, triethanolamine cornamphopropionate, triethanolamine lauraminopropionate, triethanolamine lauroamphoacetate, triethanolamine lauroamphohydroxypropylsulfonate, triethanolamine lauroamphopropionate, triethanolamine cornamphopropionate, triethanolamine lauriminodipropionate, cocoamphodipropionic acid, disodium caproamphodiacetate, disodium caproamphoadipropionate, disodium caprylоamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof.

The composition may comprises a zwitterionic co-surfactant, wherein the zwitterionic surfactant is a derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant can be selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, cetyl betaine, and mixtures thereof.

Non-limiting examples of betaine surfactants can include coco dimethyl carboxymethyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof.

Examples of sulfobetaines can include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

Suitable nonionic surfactants for use in the present invention include those described in McCutcheion's Detergents and Emulsifiers, North American edition (1986), Allured Publishing Corp., and McCutcheion's Functional Materials, North American edition (1992). Suitable nonionic surfactants for use in the personal care compositions of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

The co-surfactant can be one or more non-ionic surfactants selected from the group consisting alkyl polyglucoside, alkyl glycoside, acyl glucamide, alkanolamides, alkoxylated amides, glyceryl esters and mixture thereof.

Non-limiting examples of acyl glucamide can include lauroyl/myristoyl methyl glucamide, capryloyl/caproyl methyl glucamide, cocoyl methyl glucamide and combinations thereof.

Non-limiting examples of alkanolamides can include Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, PPG-2 Hydroxyethyl Isostearamide and mixtures thereof.

Non-limiting examples of alkoxylated amides can include PPG-2 Cocamide, PPG-2 Hydroxyethyl Cocamide, PPG-2 Hydroxyethyl Isostearamide and combinations thereof.

Representative polyoxyethylenated alcohols include alkyl chains ranging in the C9-C16 range and having from about 1 to about 110 alkoxy groups including, but not limited to, laureth-3, laureth-23, ceteth-10, steareth-10, steareth-100, beheneth-10, and commercially available from Shell Chemicals, Houston, Texas under the trade names Neodol® 91, Neodol® 23, Neodol® 25, Neodol® 45, Neodol® 135, Neodol® 67, Neodol® PC 100, Neodol® PC 200, Neodol® PC 600, and mixtures thereof.

Also available commercially are the polyoxyethylene fatty ethers available commercially under the Brij® trade name from Uniqema, Wilmington, Delaware, including, but not limited to, Brij® 30, Brij® 35, Brij® 52, Brij® 56, Brij® 58, Brij® 72, Brij® 76, Brij® 78, Brij® 93, Brij® 97, Brij® 98, Brij® 721 and mixtures thereof.

Suitable alkyl glycosides and alkyl polyglucosides can be represented by the formula (S)n-O—R wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, lauryl alcohol, myristyl alcohol, cetyl alcohol, stearyl alcohol, oleyl alcohol, and the like. Examples of these surfactants include alkyl polyglucosides wherein S is a glucose moiety, R is a C8-20 alkyl group, and n is an integer of from about 1 to about 9. Non-limiting examples of alkyl polyglucosides can include decyl glucoside, coco-glucoside, lauryl glucoside and combination thereof. Commercially available examples of these surfactants include decyl polyglucoside and lauryl polyglucoside available under trade names APG® 325 CS, APG® 600 CS and APG® 625 CS) from Cognis, Ambler, Pa. Also useful herein are sucrose ester surfactants such as sucrose cocoate and sucrose laurate and alkyl polyglucosides available under trade names Triton™ BG-10 and Triton™ CG-110 from The Dow Chemical Company, Houston, Tx.

Other nonionic surfactants suitable for use in the present invention are glyceryl esters and polyglyceryl esters, including but not limited to, glyceryl monoesters, glyceryl monoesters of C12-22 saturated, unsaturated and branched chain fatty acids such as glyceryl oleate, glyceryl monostearate, glyceryl monopalmitate, glyceryl monobehenate, and mixtures thereof, and polyglyceryl esters of C12-22 saturated, unsaturated and branched chain fatty acids, such as polyglyceryl-4 isostearate, polyglyceryl-3 oleate, polyglyceryl-2-sesquioleate, triglyceryl diisostearate, diglyceryl monooleate, tetraglyceryl monooleate, and mixtures thereof. Non-limiting examples of glyceryl esters can include glyceryl caprylate, glyceryl caprate, glyceryl cocoate, glyceryl laurate, and combinations thereof.

Also useful herein as nonionic surfactants are sorbitan esters. Sorbitan esters of C12-22 saturated, unsaturated, and branched chain fatty acids are useful herein. These sorbitan esters usually comprise mixtures of mono-, di-, tri-, etc. esters. Representative examples of suitable sorbitan esters include sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), and sorbitan isostearate.

Also suitable for use herein are alkoxylated derivatives of sorbitan esters including, but not limited to, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), and mixtures thereof, all available from Uniqema.

Also suitable for use herein are alkylphenol ethoxylates including, but not limited to, nonylphenol ethoxylates (Tergitol™ NP-4, NP-6, NP-7, NP-8, NP-9, NP-10, NP-11, NP-12, NP-13, NP-15, NP-30, NP-40, NP-50, NP-55, NP-70 available from The Dow Chemical Company, Houston, Tx.) and octylphenol ethoxylates (Triton™ X-15, X-35, X-45, X-114, X-100, X-102, X-165, X-305, X-405, X-705 available from The Dow Chemical Company, Houston, TX).

Also suitable for use herein are tertiary alkylamine oxides including lauramine oxide and cocamine oxide.

Non limiting examples of other anionic, zwitterionic, amphoteric, and non-ionic additional surfactants suitable for use in the hair care composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

Suitable surfactant combinations comprise an average weight % of alkyl branching of from about 0.5% to about 30%, alternatively from about 1% to about 25%, alternatively from about 2% to about 20%. The surfactant combination can have a cumulative average weight % of C8 to C12 alkyl chain lengths of from about 7.5% to about 25%, alternatively from about 10% to about 22.5%, alternatively from about 10% to about 20%. The surfactant combination can have an average C8-C12/C13-C18 alkyl chain ratio from about 3 to about 200, alternatively from about 25 to about 175.5, alternatively from about 50 to about 150, alternatively from about 75 to about 125.

Cationic Polymer

The hair care composition also comprises a cationic polymer. These cationic polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic polymer can be a mixture of cationic polymers.

The hair care composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

In the present invention, the cationic polymer, may be, including but not limited, to a cationic guar polymer, has a weight average Molecular weight of less than 2.2 million g/mol, or from about 150 thousand to about 2.2 million g/mol, or from about 200 thousand to about 2.2 million g/mol, or from about 250 thousand to about 2.5 million g/mol, or from about 300 thousand to about 1.2 million g/mol, or from about 700,000 thousand to about 1 million g/mol. Further, the cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.8 meq/g.

The cationic guar polymer may have a weight average Molecular weight of less than about 1.5 million g/mol, and has a charge density of from about 0.1 meq/g to about 2.5 meq/g. The cationic guar polymer may have a weight average molecular weight of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol. from about 150 thousand to about 800 thousand g/mol, or from about 200 thousand to about 700 thousand g/mol, or from about 300 thousand to about 700 thousand g/mol, or from about 400 thousand to about 600 thousand g/mol. The cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.5 meq/g.

The cationic guar polymer may be formed from quaternary ammonium compounds. The quaternary ammonium compounds for forming the cationic guar polymer may conform to the general formula 1:

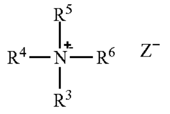

wherein where $R^3$, $R^4$ and $R^5$ are methyl or ethyl groups; $R^6$ is either an epoxyalkyl group of the general formula 2:

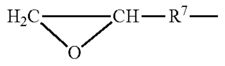

or $R^6$ is a halohydrin group of the general formula 3:

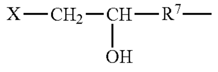

wherein $R^7$ is a $C_1$ to $C_3$ alkylene; X is chlorine or bromine, and Z is an anion such as Cl—, Br—, I— or $HSO_4$—.

The cationic guar polymer may conform to the general formula 4:

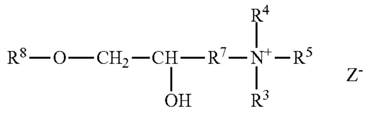

wherein $R^8$ is guar gum; and wherein $R^4$, $R^5$, $R^6$ and $R^7$ are as defined above; and wherein Z is a halogen. The cationic guar polymer may conform to Formula 5:

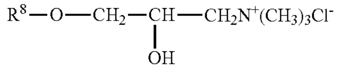

Suitable cationic guar polymers include cationic guar gum derivatives, such as guar hydroxypropyltrimonium chloride. The cationic guar polymer may be a guar hydroxypropyltrimonium chloride. Specific examples of guar hydroxypropyltrimonium chlorides include the Jaguar® series commercially available from Solvay, for example Jaguar® C-500, commercially available from Solvay. Jaguar® C-500 has a charge density of 0.8 meq/g and a molecular weight of 500,000 g/mol. Other suitable guar hydroxypropyltrimonium chloride are: guar hydroxypropyltrimonium chloride which has a charge density of about 1.3 meq/g and a molecular weight of about 500,000 g/mol and is available from Solvay as Jaguar® Optima. Other suitable guar hydroxypropyltrimonium chloride are: guar hydroxypropyltrimonium chloride which has a charge density of about 0.7 meq/g and a molecular weight of about 1,500,000 g/mol and is available from Solvay as Jaguar® Excel. Other suitable guar hydroxypropyltrimonium chloride are: guar hydroxypropyltrimonium chloride which has a charge density of about 1.1 meq/g and a molecular weight of about 500,000 g/mol and is available from ASI, a charge density of about 1.5 meq/g and a molecular weight of about 500,000 g/mole is available from ASI. Other suitable guar hydroxypropyltrimonium chloride are: Hi-Care 1000, which has a charge density of about 0.7 meq/g and a Molecular weight of about 600,000 g/mole and is available from Solvay; N-Hance 3269 and N-Hance 3270, which have a charge density of about 0.7 meq/g and a molecular weight of about 425,000 g/mol and are available from ASI; N-Hance 3196, which has a charge density of about 0.8 meq/g and a molecular weight of about 1,100,000 g/mol and is available from ASI. AquaCat CG518 has a charge density of about 0.9 meq/g and a Molecular weight of about 50,000 g/mol and is available from ASI. BF-13, which is a borate (boron) free guar of charge density of about 1.1 meq/g and molecular weight of about 800,000 and BF-17, which is a borate (boron) free guar of charge density of about 1.5 meq/g and M. Wt. of about 800,000 both available from ASI.

The hair care compositions of the present invention may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and also is affected by climate. Non-guar galactomannan polymer derivatives of the present invention have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and *Cassia* gum (5 parts mannose/1 part galactose).

The non-guar galactomannan polymer derivatives may have a M. Wt. from about 1,000 to about 10,000,000, and/or from about 5,000 to about 3,000,000.

The hair care compositions of the invention can also include galactomannan polymer derivatives which have a cationic charge density from about 0.5 meq/g to about 7 meq/g. The galactomannan polymer derivatives may have a cationic charge density from about 1 meq/g to about 5 meq/g. The degree of substitution of the cationic groups onto the galactomannan structure should be sufficient to provide the requisite cationic charge density.

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

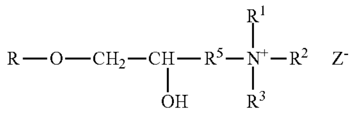

wherein R is the gum. The cationic galactomannan derivative can be a gum hydroxypropyltrimethylammonium chloride, which can be more specifically represented by the general formula 7:

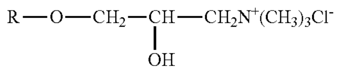

Alternatively, the galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose is greater than about 4:1, a molecular weight of about 1,000 g/mol to about 10,000,000 g/mol, and/or from about 50,000 g/mol to about 1,000,000 g/mol, and/or from about 100,000 g/mol to about 900,000 g/mol, and/or from about 150,000 g/mol to about 400,000 g/mol and a cationic charge density from about 1 meq/g to about 5 meq/g, and/or from 2 meq/g to about 4 meq/g and can be derived from a *Cassia* plant.

The hair care compositions can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The cationically modified starch polymers disclosed herein have a percent of bound nitrogen of from about 0.5% to about 4%.

The cationically modified starch polymers for use in the hair care compositions can have a molecular weight about 850,000 g/mol to about 1,500,000 g/mol and/or from about 900,000 g/mol to about 1,500,000 g/mol.

The hair care compositions can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

The cationically modified starch polymers can be selected from degraded cationic maize starch, cationic tapioca, cationic potato starch, and mixtures thereof. Alternatively, the cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance of about 80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in hair care compositions are available from known starch suppliers. Also suitable for use in hair care compositions are nonionic modified starch that can be further derivatized to a cationically modified starch as is known in the art. Other suitable modified starch starting materials may be quaternized, as is known in the art, to produce the cationically modified starch polymer suitable for use in hair care compositions.

Starch Degradation Procedure: a starch slurry can be prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

The hair care composition can comprise a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

The cationic copolymer can comprise:

(i) an acrylamide monomer of the following Formula AM:

Formula AM

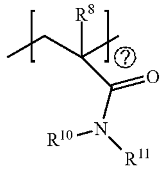

where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula CM:

Formula CM

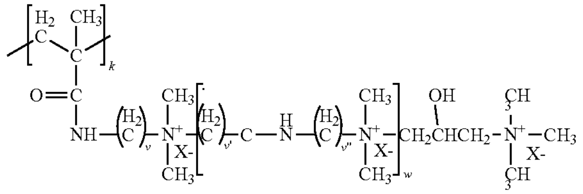

where k=1, each of v, v', and v" is independently an integer of from 1 to 6, w is zero or an integer of from 1 to 10, and $X^-$ is an anion.

The cationic monomer can conform to Formula CM and where k=1, v=3 and w=0, z=1 and $X^-$ is $Cl^-$ to form the following structure:

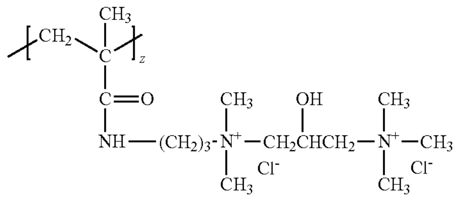

The above structure may be referred to as diquat. Alternatively, the cationic monomer can conform to Formula CM and wherein v and v" are each 3, v'=1, w=1, y=1 and $X^-$ is $Cl^-$, such as:

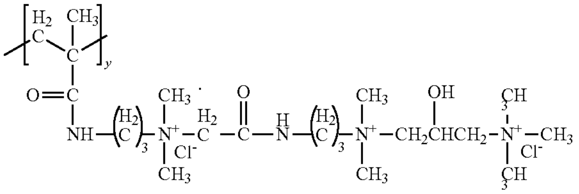

The above structure may be referred to as triquat.

Suitable acrylamide monomer include, but are not limited to, either acrylamide or methacrylamide.

The cationic copolymer (b) can be AM:TRIQUAT which is a copolymer of acrylamide and 1,3-Propanediaminium, N-[2-[[[dimethyl [3-[(2-methyl-1-oxo-2-propenyl)amino] propyl]ammonio]acetyl]amino]ethyl]2-hydroxy-N,N,N',N', N'-pentamethyl-, trichloride. AM:TRIQUAT is also known as polyquaternium 76 (PQ76). AM:TRIQUAT may have a charge density of 1.6 meq/g and a molecular weight of 1.1 million g/mol.

Further, the cationic copolymer may be of an acrylamide monomer and a cationic monomer, wherein the cationic monomer is selected from the group consisting of: dimethylaminoethyl (meth)acrylate, dimethylaminopropyl (meth) acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth) acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can comprise a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer is formed from (1) copolymers of (meth) acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. The cationized esters of the (meth) acrylic acid containing a quaternized N atom may be quaternized dialkylaminoalkyl (meth)acrylates with C1 to C3 in the alkyl and alkylene groups. Suitable cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth) acrylate; and diethylaminopropyl (meth)acrylate quaternized with methyl chloride. The cationized esters of the (meth)acrylic acid containing a quaternized N atom may be dimethylaminoethyl acrylate, which is quaternized with an alkyl halide, or with methyl chloride or benzyl chloride or dimethyl sulfate (ADAME-Quat), the cationic monomer when based on (meth)acrylamides can be quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

Suitable cationic monomer based on a (meth)acrylamide include quaternized dialkylaminoalkyl(meth)acrylamide with C1 to C3 in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

The cationic copolymer can have a molecular weight from about 100 thousand g/mol to about 1.5 million g/mol, or from about 300 thousand g/mol to about 1.5 million g/mol, or from about 500 thousand g/mol to about 1.5 million g/mol, or from about 700 thousand g/mol to about 1.0 million g/mol, or from about 900 thousand g/mol to about 1.2 million g/mol.

The cationic copolymer can be a trimethylammoniopropylmethacrylamide chloride-N-Acrylamide copolymer, which is also known as AM:MAPTAC. AM:MAPTAC may have a charge density of about 1.3 meq/g and a molecular weight of about 1.1 million g/mol. The cationic copolymer can be AM:ATPAC. AM:ATPAC can have a charge density of about 1.8 meq/g and a molecular weight of about 1.1 million g/mol.

(a) Cationic Synthetic Polymers

The hair care composition can comprise a cationic synthetic polymer that may be formed from i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers.

The cationic polymers can be water soluble or dispersible, non-crosslinked, and synthetic cationic polymers having the following structure:

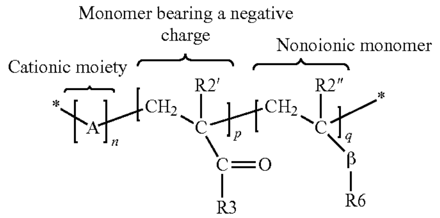

m ≥ 1
p = 0 or ≥ 1
q = 0 or ≥ 1
m ≥ p where A, may be one or more of the following cationic moieties:

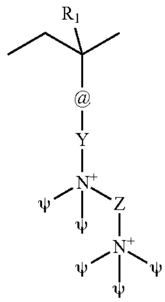

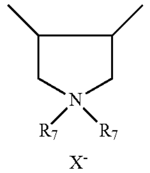

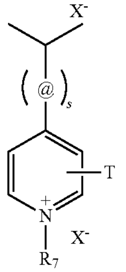

where @=amido, alkylamido, ester, ether, alkyl or alkylaryl;

where Y=C1-C22 alkyl, alkoxy, alkylidene, alkyl or aryloxy;

where ψ=C1-C22 alkyl, alkyloxy, alkyl aryl or alkyl aryloxy;

where Z=C1-C22 alkyl, alkyloxy, aryl or aryloxy;

where R1=H, C1-C4 linear or branched alkyl;

where s=0 or 1, n=0 or 1;

where T and R7=C1-C22 alkyl; and where X—=halogen, hydroxide, alkoxide, sulfate or alkylsulfate.

Where the monomer bearing a negative charge is defined by R2'=H, C1-C4 linear or branched alkyl and R3 as:

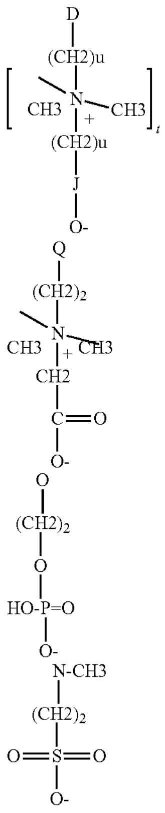

where D=O, N, or S;

where Q=NH2 or O;

where u=1-6;

where t=0-1; and where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

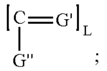 ;

and where G' and G" are, independently of one another, O, S or N—H and L=0 or 1.

Examples of cationic monomers include aminoalkyl (meth)acrylates, (meth)aminoalkyl (meth)acrylamides;

monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth) acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth) acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula $—NR_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X—) in association with the synthetic cationic polymers may be any known counterion so long as the polymers remain soluble or dispersible in water, in the hair care composition, or in a coacervate phase of the hair care composition, and so long as the counterions are physically and chemically compatible with the essential components of the hair care composition or do not otherwise unduly impair product performance, stability or aesthetics. Non limiting examples of such counterions include halides (e.g., chlorine, fluorine, bromine, iodine), sulfate and methylsulfate.

The cationic polymer described herein can aid in providing damaged hair, particularly chemically treated hair, with a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer returns the hair to a generally virgin-like, healthier state. Lyotropic liquid crystals are formed by combining the synthetic cationic polymers described herein with the aforementioned anionic detersive surfactant component of the hair care composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in WO 94/06403 to Reich et al. The synthetic polymers described herein can be formulated in a stable hair care composition that provides improved conditioning performance, with respect to damaged hair.

Cationic synthetic polymers that can form lyotropic liquid crystals may have a cationic charge density of from about 2 meq/gm to about 7 meq/gm, and/or from about 3 meq/gm to about 7 meq/gm, and/or from about 4 meq/gm to about 7 meq/gm. The cationic charge density may be about 6.2 meq/gm. The polymers also have a M. Wt. of from about 1,000 to about 5,000,000, and/or from about 10,000 to about 1,500,000, and/or from about 100,000 to about 1,500,000.

The cationic synthetic polymers that provide enhanced conditioning and deposition of benefit agents but do not necessarily form lyotropic liquid crystals may have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M. Wt. of from about 1,000 to about 1,500,000, from about 10,000 to about 1,500,000, and from about 100,000 to about 1,500,000.

Suitable cationic cellulose polymers are salts of hydroxyethyl cellulose reacted with trimethyl ammonium substituted epoxide, referred to in the industry (CTFA) as Polyquaternium 10 and available from Dow/Amerchol Corp. (Edison, N.J., USA) in their Polymer LR, JR, and KG series of polymers. Non-limiting examples include: JR-400, JR-125, JR-30M, KG-30M, JP, LR-400 and mixtures thereof. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Suitable cationic cellulose polymers may have a cationic charge density of from about 0.5 meq/gm to about 2.5 meq/gm, and/or from about 0.6 meq/gm to about 2.2 meq/gm, and/or from about 0.6 meq/gm to about 2.0 meq/gm. Further, the cationic charge density may be about 1.9 meq/gm. The polymers also have a M. Wt. of from about 200,000 to about 3,000,000, and/or from about 300,000 to about 2,200,000, from about 1,000,000 to about 2,200,000 and/or from about 300,000 to about 1,500,000. The cationic cellulose polymer may have a cationic charge density of about 1.7 to about 2.1 meq/gm and a molecular weight of from about 1,000,000 to about 2,000,000.

The concentration of the cationic polymers ranges from about 0.08% to about 3%, from about 0.1% to about 2%, and/or from about 0.2% to about 1%, by weight of the hair care composition.

Thickening Polymer

The hair care composition may comprise a thickening polymer to increase the viscosity of the composition. Suitable thickening polymers can be used. The hair care composition may comprise from about 0.1% to about 10% of a thickening polymer, from about 0.25% to about 10% of a thickening polymer, from about 0.01% to about 5%, from about 0.5% to about 8% of a thickening polymer, from about 1.0% to about 5% of a thickening polymer, and from about 1% to about 4% of a thickening polymer. The thickening polymer modifier may be a polyacrylate, polyacrylamide thickeners. The thickening polymer may be an anionic thickening polymer.

The hair care composition may comprise thickening polymers that are homopolymers based on acrylic acid, methacrylic acid or other related derivatives, non-limiting examples include polyacrylate, polymethacrylate, polyethylacrylate, and polyacrylamide.

The thickening polymers may be alkali swellable and hydrophobically-modified acrylic copolymers or methacrylate copolymers, non-limiting examples include acrylic acid/acrylonitrogens copolymer, acrylates/steareth-20 itaconate copolymer, acrylates/ceteth-20 itaconate copolymer, Acrylates/Aminoacrylates/C10-30 Alkyl PEG-20 Itaconate Copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, Acrylates/Palmeth-25 Acrylate Copolymer, Acrylic Acid/Acrylamidomethyl Propane Sulfonic Acid Copolymer, and acrylates/C10-C30 alkyl acrylate crosspolymer.

The thickening polymers may be soluble crosslinked acrylic polymers, a non-limiting example includes carbomers.

The thickening polymers may be an associative polymeric thickener, non-limiting examples include: hydrophobically modified, alkali swellable emulsions, non-limiting examples include hydrophobically modified polypolyacrylates; hydrophobically modified polyacrylic acids, and hydrophobically modified polyacrylamides; hydrophobically modified polyethers wherein these materials may have a hydrophobe that can be selected from cetyl, stearyl, oleayl, and combinations thereof.

The thickening polymers may be polyvinylpyrrolidone, crosslinked polyvinylpyrrolidone and derivatives. The thickening polymers may be polyvinyalcohol and derivatives. The thickening polymers may be polyethyleneimine and derivatives.

The thickening polymers may be alginic acid based materials, non-limiting examples include sodium alginate, and alginic acid propylene glycol esters.

The thickening polymers may be polyurethane polymers, non-limiting examples include: hydrophobically modified alkoxylated urethane polymers, non-limiting examples include PEG-150/decyl alcohol/SMDI copolymer, PEG-150/stearyl alcohol/SMDI copolymer, polyurethane-39.

The thickening polymers may be associative polymeric thickeners, non-limiting examples include: hydrophobically modified cellulose derivatives; and a hydrophilic portion of repeating ethylene oxide groups with repeat units from about 10 to about 300, from about 30 to about 200, from about 40 to about 150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

The thickening polymers may be cellulose and derivatives, non-limiting examples include microcrystalline cellulose, carboxymethylcelluloses, hydroxyethylcellulose, hydroxypropylcellulose, hydroxypropyl methylcellulose, methylcellulose, ethyl cellulose; nitro cellulose; cellulose sulfate; cellulose powder; hydrophobically modified celluloses.

The thickening polymers may be a guar and guar derivatives, non-limiting examples include hydroxypropyl guar, and hydroxypropyl guar hydroxypropyltrimonium chloride.

The thickening polymers may be polyethylene oxide; polypropylene oxide; and POE-PPO copolymers.

The thickening polymers may be combined with polyalkylene glycols characterized by the general formula:

$$\mathrm{H(OCH_2\underset{\displaystyle R}{\underset{|}{C}}H)_n{-}OH}$$

wherein R is hydrogen, methyl, or mixtures thereof, and further hydrogen, and n is an integer having an average from 2,000-180,000, or from 7,000-90,000, or from 7,000-45,000. Non-limiting examples of this class include PEG-7M, PEG-14M, PEG-23M, PEG-25M, PEG-45M, PEG-90M, or PEG-100M.

The thickening polymers may be silicas, non-limiting examples include fumed silica, precipitated silica, and silicone-surface treated silica.

The thickening polymers may be water-swellable clays, non-limiting examples include laponite, bentolite, montmorilonite, smectite, and hectonite.

The thickening polymers may be gums, non-limiting examples include xanthan gum, guar gum, hydroxypropyl guar gum, Arabia gum, tragacanth, galactan, carob gum, karaya gum, and locust bean gum.

The thickening polymers may be dibenzylidene sorbitol, karaggenan, pectin, agar, quince seed (*Cydonia oblonga* Mill), starch (from rice, corn, potato, wheat, etc), starch-derivatives (e.g. carboxymethyl starch, methylhydroxypropyl starch), algae extracts, dextran, succinoglucan, and pulleran.

Non-limiting examples of thickening polymers include acrylamide/ammonium acrylate copolymer (and) polyisobutene (and) polysorbate 20; acrylamide/sodium acryloyldimethyl taurate copolymer/isohexadecane/polysorbate 80, ammonium acryloyldimethyltaurate/VP copolymer, Sodium Acrylate/Sodium Acryloyldimethyl Taurate Copolymer, acrylates copolymer, Acrylates Crosspolymer-4, Acrylates Crosspolymer-3, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil; carbomer, sodium carbomer, crosslinked polyvinylpyrrolidone (PVP), polyacrylamide/C13-14 isoparaffin/laureth-7, polyacrylate 13/polyisobutene/polysorbate 20, polyacrylate crosspolymer-6, polyamide-3, polyquaternium-37 (and) hydrogenated polydecene (and) trideceth-6, Acrylamide/Sodium Acryloyldimethyltaurate/Acrylic Acid Copolymer, sodium acrylate/acryloyldimethyltaurate/dimethylacrylamide, crosspolymer (and) isohexadecane (and) polysorbate 60, sodium polyacrylate. Exemplary commercially-available thickening polymers include ACULYN™ 28, ACULYN™ 33, ACULYN™ 88, ACULYN™ 22, ACULYN™ Excel, Carbopol® Aqua SF-1, Carbopol® ETD 2020, Carbopol® Ultrez 20, Carbopol® Ultrez 21, Carbopol® Ultrez 10, Carbopol® Ultrez 30, Carbopol® 1342, Carbopol® Aqua SF-2 Polymer, Sepigel™ 305, Simulgel™ 600, Sepimax Zen, Carbopol® SMART 1000, Rheocare® TTA, Rheomer® SC-Plus, STRUCTURE® PLUS, Aristoflex® AVC, Stabylen 30 and combinations thereof.

Gel Network

In the present invention, a gel network may be present. The gel network component of the present invention comprises at least one fatty amphiphile. As used herein, "fatty amphiphile" refers to a compound having a hydrophobic tail group as defined as an alkyl, alkenyl (containing up to 3 double bonds), alkyl aromatic, or branched alkyl group of $C_{12}$-$C_{70}$ length and a hydrophilic head group which does not make the compound water soluble, wherein the compound also has a net neutral charge at the pH of the shampoo composition.

The shampoo compositions of the present invention comprise fatty amphiphile as part of the pre-formed dispersed gel network phase in an amount from about 0.05% to about 14%, from about 0.5% to about 10%, and from about 1% to about 8%, by weight of the shampoo composition.

According to the present invention, suitable fatty amphiphiles, or suitable mixtures of two or more fatty amphiphiles, have a melting point of at least about 27° C. The melting point, as used herein, may be measured by a standard melting point method as described in U.S. Pharmacopeia, USP-NF General Chapter <741>"Melting range or temperature". The melting point of a mixture of two or more materials is determined by mixing the two or more materials at a temperature above the respective melt points and then allowing the mixture to cool. If the resulting composite is a homogeneous solid below about 27° C., then the mixture has a suitable melting point for use in the present invention. A mixture of two or more fatty amphiphiles, wherein the mixture comprises at least one fatty amphiphile having an individual melting point of less than about 27° C., still is suitable for use in the present invention provided that the composite melting point of the mixture is at least about 27° C.

Suitable fatty amphiphiles of the present invention include fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxylated amines, fatty carbamates, fatty amine oxides, fatty acids, alkoxylated fatty acids, fatty diesters, fatty sorbitan esters, fatty sugar esters, methyl glucoside esters, fatty glycol esters, mono, di & tri glycerides, polyglycerine fatty esters, alkyl glyceryl ethers, propylene glycol fatty acid esters, cholesterol, ceramides, fatty silicone waxes, fatty glucose amides, and phospholipids and mixtures thereof.

The shampoo composition may comprise fatty alcohol gel networks. These gel networks are formed by combining fatty alcohols and surfactants in the ratio of from about 1:1 to about 40:1, from about 2:1 to about 20:1, and/or from about 3:1 to about 10:1. The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. The gel network contributes a stabilizing benefit to cosmetic creams and hair conditioners. In addition, they deliver conditioned feel benefits for hair conditioners.

The fatty alcohol can be included in the fatty alcohol gel network at a level by weight of from about 0.05 wt % to about 14 wt %. For example, the fatty alcohol may be present in an amount ranging from about 1 wt % to about 10 wt %, and/or from about 6 wt % to about 8 wt %.

The fatty alcohols useful herein include those having from about 10 to about 40 carbon atoms, from about 12 to about 22 carbon atoms, from about 16 to about 22 carbon atoms, and/or about 16 to about 18 carbon atoms. These fatty alcohols can be straight or branched chain alcohols and can be saturated or unsaturated. Nonlimiting examples of fatty alcohols include cetyl alcohol, stearyl alcohol, behenyl alcohol, and mixtures thereof. Mixtures of cetyl and stearyl alcohol in a ratio of from about 20:80 to about 80:20 are suitable.

Gel network preparation: A vessel is charged with water and the water is heated to about 74° C. Cetyl alcohol, stearyl alcohol, and SLES surfactant are added to the heated water. After incorporation, the resulting mixture is passed through a heat exchanger where the mixture is cooled to about 35° C. Upon cooling, the fatty alcohols and surfactant crystallized to form a crystalline gel network. Table 1 provides the components and their respective amounts for an example gel network composition.

TABLE 1

| Gel network components | |
|---|---|
| Ingredient | Wt. % |
| Water | 78.27% |
| Cetyl Alcohol | 4.18% |
| Stearyl Alcohol | 7.52% |
| Sodium laureth-3 sulfate (28% Active) | 10.00% |
| 5-Chloro-2-methyl-4-isothiazolin-3-one, Kathon CG | 0.03% |

Water Miscible Solvents

The carrier useful in the hair care composition may include water and water solutions of lower alkyl alcohols, polyhydric alcohols, ketones having from 3 to 4 carbons atoms, C1-C6 esters of C1-C6 alcohols, sulfoxides, amides, carbonate esters, ethoxylated and proposylated C1-C10 alcohols, lactones, pyrolidones, and mixtures thereof. Non-limited lower alkyl alcohol examples are monohydric alcohols having 1 to 6 carbons, such as ethanol and isopropanol. Non-limiting examples of polyhydric alcohols useful herein include propylene glycol, dipropylene glycol, butylenes glycol, hexylene glycol, glycerin, propane diol and mixtures thereof.

The hair care composition may comprise a hydrotrope/viscosity modifier which is an alkali metal or ammonium salt of a lower alkyl benzene sulphonate such as sodium xylene sulphonate, sodium cumene sulphonate or sodium toluene sulphonate.

The hair care composition may comprise silicone/PEG-8 silicone/PEG-9 silicone/PEG-n silicone/silicone ether (n could be another integer), non-limiting examples include PEGS-dimethicone A208) MW 855, PEG 8 Dimethicone D208 MW 2706.

Soluble Anti-Dandruff Agent

Anti-dandruff agent may be one material or a mixture selected from the groups consisting of: azoles, such as climbazole, ketoconazole, itraconazole, econazole, and elubiol; hydroxy pyridones, such as octopirox (piroctone olamine), ciclopirox, rilopirox, and MEA-Hydroxyoctyloxypyridinone; kerolytic agents, such as salicylic acid and other hydroxy acids; strobilurins such as azoxystrobin and metal chelators such as 1,10-phenanthroline.

In the present invention, the azole anti-microbials may be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. The azole anti-microbial agent may be ketoconazole. Further, the sole anti-microbial agent may be ketoconazole.

The soluble anti-dandruff agent may be present in an amount from about 0.01% to 10%, from about 0.02% to 8%, from about 0.5% to about 5%. The soluble antidandruff agent can be surfactant soluble and thus surfactant soluble antidandruff agents.

Scalp Health Agents

In the present invention, one or more scalp health agent may be added to provide scalp benefits in addition to the anti-fungal/anti-dandruff efficacy provided by the surfactant soluble anti-dandruff agents. This group of materials is varied and provides a wide range of benefits including moisturization, barrier improvement, anti-fungal, anti-microbial and anti-oxidant, anti-itch, and sensates, and additional anti-dandruff agents such as polyvalent metal salts of pyrithione, non-limiting examples include zinc pyrithione (ZPT) and copper pyrithione, sulfur, or selenium sulfide. Such scalp health agents include but are not limited to: vitamin E and F, salicylic acid, niacinamide, caffeine, panthenol, zinc oxide, zinc carbonate, basic zinc carbonate, glycols, glycolic acid, PCA, PEGs, erythritol, glycerin, triclosan, lactates, hyaluronates, allantoin and other ureas, betaines, sorbitol, glutamates, xylitols, menthol, menthyl lactate, iso cyclomone, benzyl alcohol, a compound comprising the following structure:

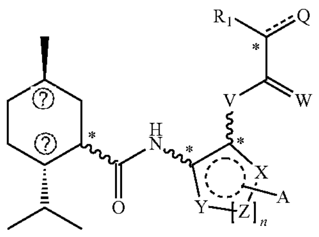

$R_1$ is selected from H, alkyl, amino alkyl, alkoxy;

Q=$H_2$, O, —$OR_1$, —$N(R_1)_2$, —$OPO(OR_1)_x$, —$PO(OR_1)_x$, —$P(OR_1)_x$ where x=1-2;

V=$NR_1$, O, —$OPO(OR_1)_x$, —$PO(OR_1)_x$, —$P(OR_1)_x$ where x=1-2;

W=$H_2$, O;

X, Y=independently selected from H, aryl, naphthyl for n=0;

X, Y=aliphatic $CH_2$ or aromatic CH for n≥1 and Z is selected from aliphatic $CH_2$, aromatic CH, or heteroatom;

A=lower alkoxy, lower alkylthio, aryl, substituted aryl or fused aryl; and stereochemistry is variable at the positions marked*.

and natural extracts/oils including peppermint, spearmint, argan, jojoba and aloe.

The scalp health agents may be present from about 0.01% to 10%, from about 0.05% to 9%, from about 0.1% to 9%, from about 0.1% to 8%, from about 0.25% to 8% and from about 0.25% to 6%.

Optional Ingredients

In the present invention, the hair care composition may further comprise one or more optional ingredients, including benefit agents. Suitable benefit agents include, but are not limited to conditioning agents, cationic polymers, silicone emulsions, anti-dandruff agents, gel networks, chelating agents, and natural oils such as sun flower oil or castor oil. Additional suitable optional ingredients include but are not limited to perfumes, perfume microcapsules, colorants, particles, anti-microbials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof. The composition may have from about 0.5% to about 7% of a perfume.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of non-limiting materials that can be added to the composition herein.

1. Conditioning Agents

The conditioning agent of the hair care compositions can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference.

The silicone conditioning agents for use in the compositions of the present invention can have a viscosity, as measured at 25° C., from about 20 to about 2,000,000 centistokes ("csk"), from about 1,000 to about 1,800,000 csk, from about 10,000 to about 1,500,000 csk, and/or from about 20,000 to about 1,500,000 csk.

The dispersed silicone conditioning agent particles typically have a volume average particle diameter ranging from about 0.01 micrometer to about 60 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the present invention include, but are not limited to, emulsions of insoluble polysiloxanes. These may be prepared via emulsion polymerization, as in accordance with the descriptions provided in U.S. Pat. No. 6,316,541 or 4,476,282 or U.S. Patent Application Publication No. 2007/0276087, or they may be emulsified after polymerization is complete, via a variety of emulsification methods as described in U.S. Pat. Nos. 9,255,184B2 or 7,683,119 or *Emulsions and Emulsion Stability*, edited by Johan Sjoblom, CRC Press, 2005. These references can be consulted for a non-limiting list of suitable emulsifiers and emulsifier blends based on the functionality of silicone used, the emulsification method, and the desired emulsion particle size. Accordingly, suitable insoluble polysiloxanes include polysiloxanes such as alpha, omega hydroxy-terminated polysiloxanes or alpha, omega alkoxy-terminated polysiloxanes having an internal phase viscosity from about 5 csk to about 500,000 csk. For example, the insoluble polysiloxane may have an internal phase viscosity less 400,000 csk; less than 200,000 csk; from about 10,000 csk to about 180,000 csk. The insoluble polysiloxane can have an average particle size within the range from about 10 nm to about 10 micron. The average particle size may be within the range from about 15 nm to about 5 micron, from about 20 nm to about 1 micron, or from about 25 nm to about 550 nm or from about 1 to 10 micron. The concentration of dispersed silicone in the emulsion may be within the range from about 5 to 90 percent, or from 20 to 85 percent, or from 30 to 80 percent by weight of the emulsion composition.

The average molecular weight of the insoluble polysiloxane, the internal phase viscosity of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscometer with spindle 6 at 2.5 rpm. The silicone emulsion may further include an additional emulsifier together with the anionic surfactant.

Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

The conditioning agent of the hair care compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

2. Emulsifiers

A variety of anionic and nonionic emulsifiers can be used in the hair care composition of the present invention. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

3. Chelating Agents

The hair care composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term includes alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440.

Chelating agents can be incorporated in the compositions herein in amounts ranging from 0.001% to 10.0% by weight of the total composition; from about 0.01% to 2.0%. Nonlimiting chelating agent classes include carboxylic acids, aminocarboxylic acids, including amino acids, phosphoric acids, phosphonic acids, polyphosphonic acids, polyethyleneimines, polyfunctionally-substituted aromatic, their derivatives and salts.

Nonlimiting chelating agents include the following materials and their salts. Ethylenediaminetetraacetic acid (EDTA), ethylenediaminetriacetic acid, ethylenediamine-N,N'-disuccinic acid (EDDS), ethylenediamine-N,N'-diglutaric acid (EDDG), salicylic acid, aspartic acid, glutamic acid, glycine, malonic acid, histidine, diethylenetriaminepentaacetate (DTPA), N-hydroxyethylethylenediaminetriacetate, nitrilotriacetate, ethylenediaminetetrapropionate, triethylenetetraaminehexaacetate, ethanoldiglycine, propylenediaminetetracetic acid (PDTA), methylglycinediacetic acid (MODA), diethylenetriaminepentaacetic acid, methylglycinediacetic acid (MGDA), N-acyl-N,N',N'-ethylenediaminetriacetic acid, nitrilotriacetic acid, ethylenediaminediglutaric acid (EDGA), 2-hydroxypropylenediamine disuccinic acid (HPDS), glycinamide-N, N'-disuccinic acid (GADS), 2-hydroxypropylenediamine-N—N'-disuccinic acid (HPDDS), N-2-hydroxyethyl-N,N-diacetic acid, glyceryliminodiacetic acid, iminodiacetic acid-N-2-hydroxypropyl sulfonic acid, aspartic acid N-carboxymethyl-N-2-hydroxypropyl-3-sulfonic acid, alanine-N,N'-diacetic acid, aspartic acid-N,N'-diacetic acid, aspartic acid N-monoacetic acid, iminodisuccinic acid, diamine-N,N'-dipolyacid, mono amide-N,N'-dipolyacid, diaminoalkyldi(sulfosuccinic acids) (DDS), ethylenediamine-N—N'-bis (ortho-hydroxyphenyl acetic acid)), N,N'-bis(2-hydroxybenzyl)ethylenediamine-N, N'-diacetic acid, ethylenediaminetetraproprionate, triethylenetetraaminehexacetate, diethylenetriaminepentaacetate, dipicolinic acid, ethylenedicysteic acid (EDC), ethylenediamine-N,N'-bis(2-hydroxyphenylacetic acid) (EDDHA), glutamic acid diacetic acid (GLDA), hexadentateaminocarboxylate (HBED), polyethyleneimine, 1-hydroxydiphosphonate, aminotri(methylenephosphonic acid) (ATMP), nitrilotrimethylenephosphonate (NTP), ethylenediaminetetramethylenephosphonate, diethylenetriaminepentamethylenephosphonate (DTPMP), ethane-1-hydroxydiphosphonate (HEDP), 2-phosphonobutane-1,2,4-tricarboxylic acid, polyphosphoric acid, sodium tripolyphosphate, tetrasodium diphosphate, hexametaphosphoric acid, sodium metaphosphate, phosphonic acid and derivatives, Aminoalkylen-poly (alkylenphosphonic acid), aminotri(1-ethylphosphonic acid), ethylenediaminetetra(1-ethylphosphonic acid), aminotri(1-propylphosphonic acid), aminotri(isopropylphosphonic acid), ethylenediaminetetra(methylenephosphonic acid) (EDTMP), 1,2-dihydroxy-3,5-disulfobenzene.

Aqueous Carrier

The hair care compositions can be in the form of pourable liquids (under ambient conditions). Such compositions will therefore typically comprise a carrier, which is present at a level of from about 40% to about 85%, alternatively from about 45% to about 80%, alternatively from about 50% to about 75% by weight of the hair care composition. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier which may be useful in the hair care compositions of the present invention may include water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

G. Product Form

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos and personal cleansing products, and treatment products; and any other form that may be applied to hair.

H. Applicator

In the present invention, the hair care composition may be dispensed from an applicator for dispensing directly to the scalp area. Dispensing directly onto the scalp via a targeted delivery applicator enables deposition of the non-diluted cleaning agents directly where the cleaning needs are highest. This also minimizes the risk of eye contact with the cleansing solution.

The applicator is attached or can be attached to a bottle containing the cleansing hair care composition. The applicator can consist of a base that holds or extends to a single or plurality of tines. The tines have openings that may be at the tip, the base or at any point between the tip and the base. These openings allow for the product to be distributed from the bottle directly onto the hair and/or scalp.

Alternatively, the applicator can also consist of brush-like bristles attached or extending from a base. In this case product would dispense from the base and the bristles would allow for product distribution via the combing or brushing motion.

Applicator and tine design and materials can also be optimized to enable scalp massage. In this case it would be beneficial for the tine or bristle geometry at the tips to be more rounded similar to the roller ball applicator used for eye creams. It may also be beneficial for materials to be smoother and softer; for example metal or metal-like finishes, "rubbery materials."

Materials and Methods

Antimicrobial Effectiveness Testing

The following method is based on United States Pharmacopeia <51>. Bacterial pools and yeast/mold pools consisting of equal parts each of *K. pneumoniae, E. gergoviae, S. marcescens, S. aureus, P. aeruginosa, E. coli*, and *B. cepacia* or *C. albicans* and *A. brasiliensis*, are inoculated into shampoo compositions as well as a saline control to deliver a target bioburden of 5.0-7.0 $\log_{10}$ cfu/ml. Following incubation at room temperature for 2 days and 7 days, inoculated compositions and the saline control are diluted in Modified Letheen broth (Becton Dickinson, Cat. No. 263010)+polysorbate 80. Solutions are pour-plated in triplicate into Tryptic Soy Agar with Lecithin and Polysorbate 80 (Becton Dickinson, Cat. No. 255320) and colony forming units (cfu) are enumerated.

Log Reduction Calculation

As shown in the sample calculations below, pour plate data are averaged then multiplied by the dilution factor to calculate the average microorganism cfu per ml. Microorganism log reduction are calculated by dividing the cfu per ml of the saline control by the cfu per ml of the composition and taking $\log_{10}$ of the quotient. Logo) of the resulting number yields the log reduction of composition over saline control. Based on the variability of the antimicrobial effectiveness test, a difference of 0.5 log reduction between compositions is considered to be a significant difference.

Alternatively, another conventional method for calculating log reduction in a composition would be to dilute the inoculum at the time of inoculation and innumerate the colonies following appropriate incubation in growth agar. The resulting cfu per ml of the inoculum would be used in place of the saline control in the numerator of the equation for calculating log reduction.

Net Change in Log Reduction Calculation

The net change in microorganism log reduction can be calculated by subtracting the log reduction of the unpreserved control from the log reduction of the shampoo composition.

Sample Calculations:

| Log Reduction | | |
|---|---|---|
| Sample | Avg. cfu | Dilution Factor |
| Shampoo Composition | 10.3 | 100 |
| Saline | 149 | 10,000 |

$$avg\ cfu/\text{mL} = avg\ cfu \times \text{dilution factor}$$

$$avg\ cfu/\text{mL of composition} = 10.3 \times 100$$

$$avg\ cfu/\text{mL of composition} = 1.03 \times 10^3$$

$$\text{log reduction} = \log_{10}\left(\frac{avg\ cfu/\text{mL of saline control}}{avg\ cfu/\text{mL of composition}}\right)$$

$$\text{log reduction} = \log_{10}\left(\frac{1.49 \times 10^6}{1.03 \times 10^3}\right)$$

$$\text{log reduction} = 3.2$$

| Net Change in Log Reduction | |
|---|---|
| Sample | Log reduction |
| Shampoo composition | 3.2 |
| Unpreserved control | −0.2 |

Net Change in Log Reduction=log reduction of composition−log reduction of unpreserved control Net Change in Log Reduction=3.2−(−0.2)

Net Change in Log Reduction=3.4

Preparation of Shampoo Compositions

The shampoo compositions are prepared by adding surfactants, anti-dandruff agents, perfume, viscosity modifiers, cationic polymers, preservatives, conditioning agents and the remainder of the water with ample agitation to ensure a homogenous mixture. The mixture can be heated to 50-75° C. to speed the solubilization of the soluble agents and hydration of cationic polymers, then cooled. Product pH may be adjusted as necessary to provide shampoo compositions of the present invention which are suitable for application to human hair and scalp, and may vary from pH about ≤6, or from about 4.5 to about 6, or from greater than 4.5 to about 6, or from about 4 to 6, or from about pH 4 to 5.8, or from about pH 4.5 to 5.8, or from greater than 4.5 to 5.8, or from 4.5 to 5.5, or from greater than 4.5 to 5.5 based on the selection of particular detersive surfactants and/or other components.

Non-Limiting Examples

The shampoo compositions illustrated in the following examples are prepared by conventional formulation and mixing methods. All exemplified amounts are listed as weight percents on an active basis and exclude minor materials such as diluents, preservatives, color solutions, imagery ingredients, botanicals, and so forth, unless otherwise specified. All percentages are based on weight unless otherwise specified.

| | Examples, active wt % | | |
|---|---|---|---|
| Ingredients | 1 (control A) | 2 | 3 |
| Sodium Laureth-1 Sulfate (SLE1S) [1] | 12.0 | 12.0 | 12.0 |
| Cocamide MEA [2] | 0.5 | 0.5 | 0.5 |
| Sodium Benzoate [3] | — | 0.11 | 0.15 |
| Sodium Salicylate [4] | — | 0.11 | 0.15 |
| Guar Hydroxypropyltrimonium Chloride [5] | 0.4 | 0.4 | 0.4 |
| Glycol Distearate [6] | 0.5 | 0.5 | 0.5 |
| Dimethiconol [7] | 1.0 | 1.0 | 1.0 |
| Acrylates Copolymer [8] | 0.7 | 0.7 | 0.7 |
| Piroctone Olamine [9] | 0.2 | 0.2 | 0.2 |
| Tetrasodium EDTA [10] | 0.13 | 0.13 | 0.13 |
| Citric Acid [11] | 0.23 | 0.23 | 0.22 |
| Fragrance | 1.0 | 1.0 | — |
| Sodium Chloride [12] | 0.86 | 0.81 | 1.29 |
| Water | q.s. | q.s. | q.s. |
| pH | 5.97 | 6.00 | 6.04 |
| 2-day bacteria log reduction | 0.8 | 3.6 | 4.0 |
| 7-day yeast/mold log reduction | 2.0 | 6.6 | 6.6 |

[1] Sodium Laureth-1 Sulfate at 26% active, supplier: P&G
[2] Ninol Comf at 85% active, supplier: Stepan
[3] Sodium Benzoate Dense NF/FCC, supplier: Emerald Performance Materials
[4] Sodium Salicylate, supplier: JQC (Huayin) Pharmaceutical Co., Ltd.
[5] N-Hance 3196, supplier: Ashland Specialty Ingredients
[6] EGDS Purified, supplier: Evonik Goldschmidt Corporation
[7] Belsil DM5500 at 42% active, supplier: Wacker
[8] Octopirox, supplier: Clariant
[9] Carbopol Aqua SF-1 at 30% active, supplier: Lubrizol
[10] Dissolvine 220-S at 84% active, supplier: Akzo Nobel
[11] Citric Acid Anhydrous, supplier: Archer Daniels Midland; level adjustable to achieve target pH
[12] Sodium Chloride, supplier: Morton; level adjustable to achieve target viscosity Discussion of Results for Examples 1-3

As noted in the method disclosure, based on the variability of the antimicrobial effectiveness test, a difference of 0.5 log reduction between compositions is considered to be a significant difference.

Examples 2 & 3 are representative compositions of the present invention. When Example 2 is compared to its unpreserved control (Example 1), the net change in bacteria log reduction is 2.8 at the 2-day timepoint and the net change in yeast/mold log reduction is 4.6 at the 7-day timepoint. When Example 3 is compared to its unpreserved control (Example 1), the net change in bacteria log reduction is 3.2 at the 2-day timepoint and the net change in yeast/mold log reduction is 4.6 at the 7-day timepoint. These net changes in log reduction represent a significant improvement in the representative compositions' anti-microbial properties over their unpreserved control and are surprising considering the low levels of benzoate and salicylate present in Examples 2 and 3.

| | Examples, active wt % | |
|---|---|---|
| Ingredients | 4 (control B) | 5 |
| Sodium Laureth-1 Sulfate (SLE1S) [1] | 11.0 | 11.0 |
| Sodium Deceth-1 Sulfate [2] | 1.0 | 1.0 |
| Cocamide MEA [3] | 0.5 | 0.5 |
| Sodium Benzoate [4] | — | 0.11 |
| Sodium Salicylate [5] | — | 0.11 |
| Guar Hydroxypropyltrimonium Chloride [6] | 0.4 | 0.4 |
| Glycol Distearate [7] | 0.5 | 0.5 |
| Dimethiconol [8] | 1.0 | 1.0 |
| Acrylates Copolymer [9] | 0.7 | 0.7 |
| Piroctone Olamine [10] | 0.2 | 0.2 |
| Tetrasodium EDTA [11] | 0.13 | 0.13 |
| Citric Acid [12] | 0.22 | 0.23 |
| Fragrance | 1.0 | 1.0 |
| Sodium Chloride [13] | 1.09 | 0.95 |
| Water | q.s. | q.s. |
| pH | 6.02 | 6.00 |
| 2-day bacteria log reduction | 1.0 | 6.3 |
| 7-day yeast/mold log reduction | 2.3 | 5.9 |

[1] Sodium Laureth-1 Sulfate at 26% active, supplier: P&G
[2] Sodium Deceth-1 Sulfate at 34% active, supplier: P&G
[3] Ninol Comf at 85% active, supplier: Stepan
[4] Sodium Benzoate Dense NF/FCC, supplier: Emerald Performance Materials
[5] Sodium Salicylate, supplier: JQC (Huayin) Pharmaceutical Co., Ltd.
[6] N-Hance 3196, supplier: Ashland Specialty Ingredients
[7] EGDS Purified, supplier: Evonik Goldschmidt Corporation
[8] Belsil DM5500 at 42% active, supplier: Wacker
[9] Octopirox, supplier: Clariant
[10] Carbopol Aqua SF-1 at 30% active, supplier: Lubrizol
[11] Dissolvine 220-S at 84% active, supplier: Akzo Nobel
[12] Citric Acid Anhydrous, supplier: Archer Daniels Midland; level adjustable to achieve target pH
[13] Sodium Chloride, supplier: Morton; level adjustable to achieve target viscosity

Discussion of Results for Examples 4-5

As noted in the method disclosure, based on the variability of the antimicrobial effectiveness test, a difference of 0.5 log reduction between compositions is considered to be a significant difference.

Examples 5 is a representative composition of the present invention. When Example 5 is compared to its unpreserved control (Example 4), the net change in bacteria log reduction is 5.3 at the 2-day timepoint and the net change in yeast/mold log reduction is 3.6 at the 7-day timepoint. These net changes in log reduction represent a significant improvement in the representative composition's anti-microbial properties over the unpreserved control and is surprising considering the low level of benzoate and salicylate present in Example 5.

| | Examples, active wt % | | |
|---|---|---|---|
| Ingredients | 6 (control C) | 7 | 8 |
| Sodium Laureth-1 Sulfate (SLE1S) [1] | 17.0 | 17.0 | 17.0 |
| Sodium Benzoate [2] | — | 0.1 | 0.1 |
| Sodium Salicylate [3] | — | 0.1 | 0.2 |
| Guar Hydroxypropyltrimonium Chloride [4] | 0.4 | 0.4 | 0.4 |
| Glycol Distearate [5] | 0.5 | 0.5 | 0.5 |
| Dimethiconol [6] | 1.0 | 1.0 | 1.0 |
| Tetrasodium EDTA [7] | 0.13 | 0.13 | 0.13 |
| Citric Acid [8] | 0.29 | 0.3 | 0.3 |
| Fragrance | 1.0 | 1.0 | 1.0 |
| Sodium Chloride [9] | 0.8 | 0.9 | 0.9 |
| Water | q.s. | q.s. | q.s. |
| pH | 6.02 | 6.02 | 6.01 |
| 2-day bacteria log reduction | −0.3 | 1.25 | 3.03 |
| 7-day yeast/mold log reduction | 0.36 | 0.94 | 1.06 |

[1] Sodium Laureth-1 Sulfate at 26% active, supplier: P&G
[2] Sodium Benzoate Dense NF/FCC, supplier: Emerald Performance Materials
[3] Sodium Salicylate, supplier: JQC (Huayin) Pharmaceutical Co., Ltd.
4 N-Hance 3196, supplier: Ashland Specialty Ingredients
[5] EGDS Purified, supplier: Evonik Goldschmidt Corporation
[6] Belsil DM5500 at 42% active, supplier: Wacker
[7] Dissolvine 220-S at 84% active, supplier: Akzo Nobel
[8] Citric Acid Anhydrous, supplier: Archer Daniels Midland; level adjustable to achieve target pH
[9] Sodium Chloride, supplier: Morton; level adjustable to achieve target viscosity

Discussion of Results for Examples 6-8

At the 2-day timepoint, the unpreserved control (Example 6) results in a negative bacteria log reduction, which is indicative of bacterial growth. As noted in the method disclosure, based on the variability of the antimicrobial effectiveness test, a net change or difference of 0.5 log reduction between compositions is considered to be a significant difference.

Examples 7 & 8 are representative compositions of the present invention. When Example 7 is compared to its unpreserved control (Example 6), the net change in bacteria log reduction is 1.8 at the 2-day timepoint and the net change in yeast/mold log reduction is 0.6 at the 7-day timepoint. When Example 8 is compared to its unpreserved control (Example 6), the net change in bacteria log reduction is 3.6 at the 2-day timepoint and the net change in yeast/mold log reduction is 0.7 at the 7-day timepoint. These net changes in log reduction represent a significant improvement in the representative compositions' anti-microbial properties over their unpreserved control and are surprising considering the low levels of benzoate and salicylate present in Examples 7 and 8.

The present invention results demonstrate a hair care composition wherein the composition provides a net change in bacteria log reduction of 0.5 or greater in comparison to an unpreserved control. The present invention results demonstrate a hair care composition wherein the composition provides a net change in yeast and/or mold log reduction of 0.5 or greater in comparison to an unpreserved control. The present invention results demonstrate a hair care composition wherein the composition provides a net change in bacteria log reduction of 0.5 or greater and yeast and/or mold log reduction of 0.5 or greater in comparison to an unpreserved control. The present invention results demonstrate a hair care composition wherein the composition provides a net change in bacteria log reduction of 0.5 or greater in comparison to an unpreserved control at the 2-day timepoint. The present invention results demonstrate a hair care composition wherein the composition provides a net change in yeast and/or mold log reduction of 0.5 or greater in comparison to an unpreserved control at the 7-day timepoint. The present invention results demonstrate a hair care composition wherein the composition provides a net change in bacteria log reduction of 0.5 or greater in comparison to an unpreserved control at the 2-day timepoint and yeast and/or mold log reduction of 0.5 or greater in comparison to an unpreserved control at the 7-day timepoint.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention

What is claimed:

1. A hair care composition comprising:

a. from about 10 to about 17%, by total weight of the composition, of one or more surfactants wherein the one or more surfactants are free of sulfate-based surfactants;

b. from about 0.1-0.25%, by total weight of the composition, of one or more salicylate salts or acids;

c. from about 0.1-0.25%, by total weight of the composition, of one of more benzoate salts or acids wherein there is a weight ratio of about 1:1 to 2.5:1 for the one or more salicylate salts or acids to one or more benzoate salts or acids.

2. A hair care composition according to claim 1 where the one or more salicylate salts or acids is from about 0.1 to 0.2%, by total weight of the composition.

3. A hair care composition according to claim 1 wherein the one or more salicylate salts or acids is from about 0.1 to 0.18%, by total weight of the composition.

4. A hair care composition according to claim 1 wherein the one or more salicylate salts or acids is sodium salicylate.

5. A hair care composition according to claim 1 wherein the one or more benzoate salts or acids is sodium benzoate.

6. A hair care composition according to claim 1 wherein the one or more benzoate salts or acids is from about 0.1 to 0.2%, by total weight of the composition.

7. A hair care composition according to claim 1 wherein the one or more benzoate salts or acids is from about 0.1 to 0.18%, by total weight of the composition.

8. A hair care composition according to claim 1 wherein there is a weight ratio of about 1:1 to 2:1 of the one or more salicylate salts or acids to the one or more benzoate salts or acids.

9. A hair car composition according to claim 1 wherein there is a weight ratio of about 1:1 to 1.5:1 of the one or more salicylate salts or acids to the one or more benzoate salts or acids.

10. A hair care composition according to claim 1 wherein there is a weight ratio of about 1:0.9 to 2:1 of the one or more salicylate salts or acids to the one or more benzoate salts or acids.

11. A hair care composition according to claim 1 wherein there is a weight ratio of about 1:0.8 to 2:1 of the one or more salicylate salts or acids to the one or more benzoate salts or acids.

12. A hair care composition according to claim 1 wherein there is a weight ratio of about 1:0.75 to 2:1 of the one or more salicylate salts or acids to the one or more benzoate salts or acids.

13. A hair care composition according to claim 1 wherein there is a weight ratio of about 1:0.8 to 1.5:1 of the one or more salicylate salts or acids to the one or more benzoate salts or acids.

14. A hair care composition according to claim 1 wherein the composition has a pH less than or equal to about 6.

15. A hair care composition according to claim 14 wherein the pH of the composition is greater than 4.5 and less than about 6.

16. A hair care composition according to claim 1 wherein the composition provides a net change in bacteria log reduction of 0.5 or greater in comparison to an unpreserved control.

17. A hair care composition according to claim 1 wherein the composition provides a net change in yeast and/or mold log reduction of 0.5 or greater in comparison to an unpreserved control.

18. A hair care composition according to claim 1 wherein the composition provides a net change in bacteria log reduction of 0.5 or greater and yeast and/or mold log reduction of 0.5 or greater in comparison to an unpreserved control.

19. A hair care composition according to claim 1 wherein the composition provides a net change in bacteria log reduction of 0.5 or greater in comparison to an unpreserved control at the 2-day timepoint.

20. A hair care composition according to claim 1 wherein the composition provides a net change in yeast and/or mold log reduction of 0.5 or greater in comparison to an unpreserved control at the 7-day timepoint.

21. A hair care composition according to claim 1 wherein the composition provides a net change in bacteria log reduction of 0.5 or greater in comparison to an unpreserved control at the 2-day timepoint and yeast and/or mold log reduction of 0.5 or greater in comparison to an unpreserved control at the 7-day timepoint.

22. A hair care composition according to claim 1 wherein the composition further comprising one or more soluble antidandruff agents.

23. A hair care composition according to claim 22 wherein the one or more soluble antidandruff agents is hydroxyl pyridone.

24. A hair care composition according to claim 23 wherein the hydroxyl pyridone is piroctone olamine.

25. A hair care composition according to claim 22 wherein the one or more soluble antidandruff agents is an azole.

26. A hair care composition according to claim 25 wherein the azole is climbazole.

27. A hair care composition according to claim 22 wherein the one or more soluble antidandruff agents is from about 0.01% to about 10%, by total weight of the composition.

28. A hair care composition according to claim 22 wherein the one or more soluble antidandruff agents is from about 0.02% to about 8%, by total weight of the composition.

29. A hair care composition according to claim 22 wherein the one or more soluble antidandruff agent is from about 0.05% to 5%, by total weight of the composition.

30. A hair care composition according to claim 1 wherein the one or more surfactants is an anionic surfactant or combinations of anionic surfactants.

31. A hair care composition according to claim 1 wherein the one or more surfactants is a surfactant or combinations of surfactants that is selected from the group consisting of amino acid based anionic surfactants, sulfosuccinates, isethionates, sulfonates, sulfoacetates, sulfolaurates, glucose carboxylates, alkyl ether carboxylates, taurates, lactates and lactylates.

32. A hair care composition according to claim 31 wherein the one or more surfactants is a surfactant or combinations of surfactants that is selected from the group consisting of anionic alkyl and alkyl ether sulfosuccinates, dialkyl and dialkyl ether sulfosuccinates, sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, alpha olefin sulfonates, linear alkylbenzene sulfonates, alkyl glyceryl sulfonates, sodium laurylglucosides hydroxypropylsulfonate, sodium lauryl sulfoacetate, ammonium lauryl sulfoacetate, sodium methyl cocoyl taurate, sodium methyl lauroyl taurate, sodium caproyl methyltaurate, sodium methyl oleoyl taurate, sodium cocoyl taurate, sodium lauroyl taurate and sodium caproyl taurate.

33. A hair care composition according to claim 1 wherein one or more surfactants is present from about 10% to about 16%, by total weight of the composition.

34. A hair care composition according to claim 1 wherein one or more surfactants is present from about 10% to about 15%, by total weight of the composition.

35. A hair care composition according to claim 1 wherein one or more surfactants is present from about 10% to about 14%, by total weight of the composition.

36. A hair care composition according to claim 1 wherein one or more surfactants is present from about 10% to about 13%, by total weight of the composition.

37. A hair care composition according to claim 1 further comprising from about 0.25% to about 15%, by total weight of the composition, of one or more amphoteric, nonionic or zwitterionic co-surfactants.

38. A hair care composition according to claim 37 wherein the one or more amphoteric, nonionic or zwitterionic co-surfactants is selected from the group consisting of betaines, lauramidopropyl betaine, cocamidopropyl betaine, cocobetaine, cetyl betaine, lauryl hydroxysultaine, sodium lauroamphoacetate, disodium cocoamphodiacetate, cocamide monoethanolamide, sultaines, hydroxysultaines, amphohydroxypropyl sulfonates, alkyl amphoacetates, alkyl polyglucosides and mixtures thereof.

39. A hair care composition according to claim 1 further comprising one or more cationic polymers selected from the group consisting of a cationic guar polymer, a cationic non-guar galactomannan polymer, a cationic tapioca polymer, a cationic copolymer of acrylamide monomers and cationic monomers, a synthetic, non-crosslinked, cationic polymer, which may or may not form lyotropic liquid crystals upon combination with the detersive surfactant, a cationic cellulose polymer and mixtures thereof.

40. A hair care composition according to claim 39 wherein the one or more cationic polymer is selected from the group consisting of guar hydroxypropyltrimonium chloride, salts of hydroxyethyl cellulose reacted with trimethyl ammonium substituted epoxide, a cationic copolymer of acrylamide monomers and cationic monomers, a synthetic, non-crosslinked, cationic polymer, which may or may not form lyotropic liquid crystals upon combination with the detersive surfactant.

41. A hair care composition according to claim 39 wherein the one or more cationic polymers is from about 0.08% to about 3%, by total weight of the composition.

42. A hair care composition according to claim 39 wherein the one of more cationic polymers is from about 0.1% to about 2%, by total weight of the composition.

43. A hair care composition according to claim 39 wherein the one of more cationic polymers is from about 0.2% to about 1%, by total weight of the composition.

44. A hair care composition according to claim 1 further comprising from about 0.01% to about 10%, by total weight of the composition, of one or more thickening polymer.

45. A hair care composition according to claim 44 wherein the one or more thickening polymer is selected from the group consisting of homopolymers based on acrylic acid, homopolymers based on methacrylic acid, derivatives of homopolymers of acrylic acid, derivatives of homopolymers of methacrylic acid, alkali swellable acrylic copolymers, hydrophobically-modified alkali swellable acrylic copolymers, alkali swellable methacrylate copolymers, hydrophobically-modified alkali swellable methacrylate copolymers, soluble crosslinked acrylic polymers, associative polymeric thickeners and mixtures thereof.

46. A hair care composition according to claim 1 further comprising one or more scalp health agents.

47. A hair care composition according to claim 46 wherein one or more scalp health agents is selected from the group consisting of sulfur, menthol, menthyl lactate and mixtures thereof.

48. A hair care composition according to claim 46 wherein the one or more scalp health agents is polyvalent metal salts of pyrithione.

49. A hair care composition according to claim 48 wherein the one or more scalp health agents is zinc pyrithione.

50. A hair care composition according to claim 46 wherein the one or more scalp health agents is from about 0.01% to 10%, by total weight of the composition.

51. A hair care composition according to claim 46 wherein the one or more scalp health agents is from about 0.05% to 9%, by total weight of the composition.

52. A hair care composition according to claim 46 wherein the one or more scalp health agents is from about 0.1% to 8%, by total weight of the composition.

* * * * *